US008483467B2

(12) United States Patent
Mizuno

(10) Patent No.: US 8,483,467 B2
(45) Date of Patent: Jul. 9, 2013

(54) MEDICAL IMAGE DIAGNOSIS ASSISTING APPARATUS AND METHOD, AND COMPUTER READABLE RECORDING MEDIUM ON WHICH IS RECORDED PROGRAM FOR THE SAME

(75) Inventor: Osamu Mizuno, Tokyo (JP)

(73) Assignee: Fujifilm Corporation, Tokyo (JP)

( * ) Notice: Subject to any disclaimer, the term of this patent is extended or adjusted under 35 U.S.C. 154(b) by 234 days.

(21) Appl. No.: 13/017,415

(22) Filed: Jan. 31, 2011

(65) Prior Publication Data

US 2011/0190626 A1    Aug. 4, 2011

(30) Foreign Application Priority Data

Jan. 31, 2010    (JP) ................. 2010-084388

(51) Int. Cl.
*G06K 9/00*    (2006.01)
(52) U.S. Cl.
USPC ........................................................ 382/131
(58) Field of Classification Search
USPC ....... 382/128–134; 128/920–925; 356/39–49; 600/407–414, 424–426; 345/581–618
See application file for complete search history.

(56) References Cited

U.S. PATENT DOCUMENTS

| | | | |
|---|---|---|---|
| 7,286,694 | B2 | 10/2007 | Oosawa |
| 7,623,695 | B2 | 11/2009 | Matsumoto |
| 7,715,608 | B2 | 5/2010 | Vaz et al. |
| 2006/0229513 | A1 | 10/2006 | Wakai |
| 2007/0092864 | A1 | 4/2007 | Reinhardt et al. |

FOREIGN PATENT DOCUMENTS

| | | |
|---|---|---|
| JP | 2005-028121 | 2/2005 |
| JP | 2008-253293 | 10/2008 |

OTHER PUBLICATIONS

"Quantification of shrinkage of lung lobes in chest CT images using the 3D Voronoi division and application to tumor discrimination" by Y. Hirano et al., [Online]. JMIT 20th annual meeting proceedings, pp. 315-316, Jul. 2001, [Date of Retrieval: Nov. 20, 2009], Internet <URL: http//mase.itc.nagoya-u.ac.Jp/ hirano/Papers JAMIT2001. pdf>.
"Quantitation of emphysema by computed tomography using a "density mask" program and correlation with pulmonary function tests" by M. Kinsella et al., Chest, vol. 97, pp. 315-321, 1990.
"A method for Extraction of Bronchus Regions from 3D Chest X-ray CT Images by Analyziing Structural Features of the Bronchus" by T. Kitasaka et al., Forma, vol. 17, pp. 321-338, 2002.

(Continued)

*Primary Examiner* — Atiba O Fitzpatrick
(74) *Attorney, Agent, or Firm* — Young & Thompson

(57) ABSTRACT

Extracting a lung field area and a branch structure area from a three-dimensional medical image, dividing a branch structure local area representing a portion of the branch structure area into a plurality of branch structure local sub-areas and estimating a lung field local sub-area in the lung field area functionally associated with each divided branch structure local sub-area based on the branch structure area, obtaining a pulmonary evaluation value in each estimated lung field local sub-area, and displaying, in a morphological image representing morphology of at least a portion of the branch structure local area, the pulmonary evaluation value in each lung field local sub-area functionally associated with each branch structure local sub-area in the morphological image superimposed such that correspondence relationship between the pulmonary evaluation value and the branch structure local sub-area in the morphological image is visually recognizable.

19 Claims, 8 Drawing Sheets

OTHER PUBLICATIONS

"Trial of branch base tree structure model construction for blood vessel geometric representation" by D. Kobayashi et al, [Online], RIKEN, Japan, RIKEN symposium, Digitization and database construction research of organism shape information, pp. 84-92, Mar. 3, 2005, [Date of Retrieval: Jan. 6, 2010], Internet <URL: http//www.comp-bio-riken.jp/keijyo/products/2005_1_files/kobayashi_print.pdf>.

"Automated Classification of Pulmonary Artery and Vein from Chest X-ray CT images by Tree Structure Analysis" by S. Nakamura et al., Technical Report of IEICE, MI Japan, vol. 105, No. 580, pp. 105-108, Jan. 21, 2006, [Date of Retrieval: Nov. 20, 2009], Internet <URL: http://www.murase.nuie.nagoya-u.ac.jp/ ide/res/paper/J05-kenkyukai-snake-1.pfd>.

"Development of the Procedure for Automatic Extrachting Interlobar Fissures and its Performance Evaluation" by T. Hayashi et al., Technical Report of IEICE, MI, Medical Image, vol. 103, No. 409, pp. 39-44, Oct. 31, 2003, [Date of Retrieval: Jan. 8, 2010], Internet, <URL: http://www.fjt.info.gifu-u.ac.jp/publication.328.pdf>.

"Complexity of terminal airspace geometry assessed by lung computed tomography in normal subjects and patients with chronic obstructive pulmonary disease" by M. Mishima et al., Proc. Natl. Acad. Sci. USA, vol. 96, pp. 8829-8834, 1999.

"Nonrigid Registration Using Free-Form Deformations: Application to Breast MR Images" by D. Rueckert et al., IEEEE Transactions on Medical Imaging, vol. 18, No. 8, pp. 712-721, 1999.

Extended European Search Report issued on Jul. 22, 2011 by the European Patent Office in corresponding European Patent Application No. 11152238.9, 7 pages.

Hirano, Y. et al., "Quantification of shrinkage of lung lobe from chest CT images using the 3D extended Voronoi division and its application to the benign/malignant discrimination of tumor shadows", Pattern Recognition, 2002. Proceedings. 16th International Conference on Quebec City, Que., Canada, Aug. 11-15, 2002, Los Alamitos, CA, USA, IEEE Comput. Soc., US, vol. 1, Aug. 11, 2002, pp. 751-754, XP010613440.

Kuhnigk, J.-M. et al., "Informatics in Radiology (infoRAD): New Tools for Computer Assistance in Thoracic CT. Part 1. Functional Analysis of Lungs, Lung Lobes, and Bronchopulmonary Segments", Radiographics, vol. 25, No. 2, Mar. 1, 2005, pp. 525-536, XP55002525.

MEDICAL IMAGE DIAGNOSIS ASSISTING APPARATUS AND METHOD, AND COMPUTER READABLE RECORDING MEDIUM ON WHICH IS RECORDED PROGRAM FOR THE SAME

BACKGROUND OF THE INVENTION

1. Field of the Invention

The present invention relates to an apparatus and method for assisting image diagnosis using a three-dimensional medical image representing a chest region of a subject. The invention also relates to a computer readable recording medium on which is recorded a program for the same.

2. Description of the Related Art

A technology for assisting pulmonary image diagnosis using a three-dimensional medical image representing a chest region is known.

For example, a method in which segmentation of pulmonary parechymal tissue is performed on a CT image representing both lungs, then a perfusion map of the segmented image is generated, and an abnormally underperfused area is rendered and displayed comparatively opaque is proposed as described, for example, in U.S. Pat. No. 7,715,608.

Another method in which lung areas are extracted from CT images representing a lung in insipiratory phase and in expiratory phase, a position alignment is performed on the extracted lung areas using a non-rigid registration method to obtain a displacement vector field in the lung area, then a regional lung volume is calculated by calculating exhalation at each point of the displacement vector field, and a state of lung ventilation distribution is visualized in an axial cross-section image or volume rendering image representing the lung based on the regional lung volume is proposed as described, for example, in Japanese Unexamined Patent Publication No. 2005-028121.

Gas exchange occurs with capillary vessel blood in an alveolus of a lung. At that time, carbon dioxide discharged from the blood is conveyed to the outside through a bronchus and oxygen conveyed from the outside through the bronchus is passed to the blood. It is, therefore, advantageous in image diagnosis of lung to interpret an evaluation value representing a perfusion or a regional lung volume in each section of a lung by considering the association with a bronchus or a blood vessel.

But, a bronchus or a blood vessel is complexly distributed over the entire lung field by repeating branching and thinning, and it is extremely difficult to interpret an evaluation value representing a perfusion or a regional lung volume in each section of a lung by considering the association with a bronchus or a blood vessel in an image representing the entirety of a lung as in the method described in each patent document above.

The present invention has been developed in view of the circumstances described above and it is an object of the present invention to provide a medical image diagnosis assisting apparatus and method that uses a three-dimensional medical image representing a chest region of a subject and allows highly accurate pulmonary image diagnosis by considering the association with a branch structure, such as a bronchus or a blood vessel. It is a further object of the present invention to provide a computer readable recording medium on which is recorded a medical image diagnosis assisting program of the present invention.

SUMMARY OF THE INVENTION

A medical image diagnosis supporting apparatus of the present invention is an apparatus, including:

a lung field area extraction means for extracting a lung field area from a three-dimensional medical image representing a chest region of a subject;

a branch structure area extraction means for extracting a branch structure area from the three-dimensional medical image;

a lung field local sub-area estimation means for dividing a branch structure local area representing a portion of the branch structure area into a plurality of branch structure local sub-areas and estimating a lung field local sub-area in the lung field area functionally associated with each divided branch structure local sub-area based on the branch structure area;

a pulmonary evaluation value obtaining means for obtaining a pulmonary evaluation value of pulmonary function and/or morphology in each estimated lung field local sub-area; and a display control means for displaying, in a morphological image representing morphology of at least a portion of the branch structure local area generated from the three-dimensional medical image, the pulmonary evaluation value in each lung field local sub-area functionally associated with each branch structure local sub-area in the morphological image superimposed such that correspondence relationship between the pulmonary evaluation value and the branch structure local sub-area in the morphological image is visually recognizable.

A medical image diagnosis supporting method of the present invention is a method, including the steps of:

extracting a lung field area from a three-dimensional medical image representing a chest region of a subject;

extracting a branch structure area from the three-dimensional medical image;

dividing a branch structure local area representing a portion of the branch structure area into a plurality of branch structure local sub-areas and estimating a lung field local sub-area in the lung field area functionally associated with each divided branch structure local sub-area based on the branch structure area;

obtaining a pulmonary evaluation value of pulmonary function and/or morphology in each estimated lung field local sub-area; and displaying, in a morphological image representing morphology of at least a portion of the branch structure local area generated from the three-dimensional medical image, the pulmonary evaluation value in each lung field local sub-area functionally associated with each branch structure local sub-area in the morphological image superimposed such that correspondence relationship between the pulmonary evaluation value and the branch structure local sub-area in the morphological image is visually recognizable.

A computer readable recording medium on which is recorded a medical image diagnosis assisting program of the present invention is a medium having a program recorded thereon for causing a computer to perform the method described above.

The term "branch structure" as used herein refers to a bronchus or a blood vessel.

As for the method of extracting a lung field area or a branch structure area, any known extraction method may be used. As a bronchus runs parallel with a pulmonary artery and the pulmonary artery appears in an image further to the periphery in comparison with the bronchus, a pulmonary artery area may be extracted as a bronchus area when a bronchus is extracted as the branch structure. Alternatively, an arrangement may be adopted in which both the bronchus and pulmonary artery are extracted and, with respect to a peripheral portion of the extracted bronchus, a portion of the pulmonary artery area from a point in the pulmonary artery area nearest to a peripheral portion of the extracted bronchus to a peripheral portion of the pulmonary artery as a bronchus area connecting to the peripheral portion of the bronchus.

The "branch structure local area" may be set by a user manual specifying operation in an image generated from the three-dimensional medical image, by automatically using an image analysis/recognition method, or by a combination thereof. Specific examples of the combined method may include a method in which a reference point of a branch structure local area is specified by a manual user operation and a predetermined image analysis/recognition process is performed based on the reference point, thereby automatically extracting the branch structure local area, a method in which a branch structure local area is selected by a user manual operation from branch structure local area candidates automatically extracted by a predetermined image analysis/recognition process, and a method in which a branch structure local area candidate is corrected by a user manual operation.

The "branch structure local sub-areas" may be, for example, those obtained by dividing the branch structure local area with respect to each branch of the branch structure or those obtained by dividing the branch structure local area at a predetermined distance. Hereinafter, the branch structure local sub-area is also referred to as the first branch structure local sub-area.

The term "(lung field local sub-area) functionally associated with (branch structure local sub-area)" as used herein refers to that a gas exchanged in the lung field local sub-area passes through the branch structure local sub-area.

It is conceivable that the "lung field local sub-area" is estimated based on morphological characteristics of the branch structure, such as the positional relationship of the branch structure area, tube diameter of the branch structure, and the like. Further, the lung represented in the three-dimensional medical image may be divided into a plurality of predetermined lung sections and the lung field local sub-area may be estimated so as to belong to one of the divided lung sections.

If the branch structure is a bronchus, a pulmonary artery area may further be extracted and the lung field local sub-area may be estimated with a portion of the pulmonary artery area from a point in the pulmonary artery area nearest to a peripheral portion of the bronchus extracted as the branch structure to a peripheral portion of the pulmonary artery being deemed as a bronchus area connecting to the peripheral portion of the bronchus.

A specific example of the "evaluation value" is a degree of emphysema in each lung field local sub-area.

Further, the "evaluation value" may be calculated based the three-dimensional medical image, the processing target image of the present invention, or an evaluation value calculated based on another medical image representing the chest region of the same subject may be obtained as the evaluation value. Here, the "another medical image" may be an image captured by the same modality as that of the three-dimensional medical image, the processing target image of the present invention, at a different time or an image captured by a different modality. Further, an evaluation value calculated based on certain measurement data with respect to the chest region of the same subject may be obtained as the evaluation value. When an evaluation value based on another medical image or measurement data are used, in particular, it is preferable that position alignment is performed so that the position of the chest region of the subject represented by the evaluation value matches with the corresponding position in the morphological image.

The "morphological image" may be an image representing morphology of a portion of a branch structure local area, like a cross-sectional image representing a cross-section of a branch structure at a given point in the branch structure local area, or an image representing morphology of the entirety of the branch structure local area. A specific example of the latter may be a CPR image representing a branch structure local area reconstructed from the three-dimensional medical image by CPR (curved planar reformation/reconstruction). Further, the morphological image may include a lung field local sub-area functionally associated with at least a portion of the branch structure local area.

A specific example of the mode of "superimposed display" may be a mode in which the evaluation value is displayed in the morphological image superimposed on a position not to overlap with the branch structure local area. For example, the evaluation value may be displayed in the morphological image superimposed on a position away from a core line of the branch structure local area by a predetermined distance. Further, when a lung field local sub-area is included in the morphological image, the evaluation value may be displayed in the morphological image superimposed on a position not to overlap with the branch structure local area and the lung field local sub-area.

Further, the branch structure local area in the morphological image may be divided into a plurality of second branch structure local sub-areas and a second evaluation value may be obtained with respect to each second branch structure local sub-area, and the second evaluation value of each second branch structure local sub-area may further be displayed superimposed on the morphological image such that correspondence relationship between the second evaluation value and the second branch structure local sub-area is visually recognizable. Here, the branch structure local area may be divided into each of the "second branch structure local sub-areas" so as to correspond to or not to correspond to each of the first branch structure local sub-areas. A specific example of the "second evaluation value" may be a measurement value of the diameter of the branch structure local area in the morphological image. When a superimposed display is performed, the second evaluation value may be displayed in the morphological image superimposed on a position not to overlap with the evaluation value of pulmonary function and/or morphology.

According to the present invention, a lung field area and a branch structure area are extracted from a three-dimensional medical image, then a branch structure local area representing a portion of the branch structure area is divided into a plurality of branch structure local sub-areas and a lung field local sub-area in the lung field area functionally associated with each divided branch structure local sub-area is estimated based on the branch structure area, a pulmonary evaluation value of pulmonary function and/or morphology in each estimated lung field local sub-area is obtained, and, in a morphological image representing morphology of at least a portion of the branch structure local area generated from the three-dimensional medical image, a pulmonary evaluation value of each lung field local sub-area functionally associated with each branch structure local sub-area in the morphological image is displayed superimposed such that correspondence relationship between the pulmonary evaluation value and the branch structure local sub-area in the morphological image is visually recognizable. This allows local observation/evaluation of a lung to be made based on the functional relationship between a local area of the branch structure and an adjacent lung field area. That is, highly accurate pulmonary image diagnosis may be made by considering the association with a branch structure.

DESCRIPTION OF THE PREFERRED EMBODIMENTS

Hereinafter, a medical image diagnosis system that employs a medical image diagnosis assisting apparatus according to an embodiment of the present invention will be described by taking, as example, the case in which pulmonary image diagnosis is performed by considering the association with a bronchus, one of branch structures of a lung.

Figure 1:
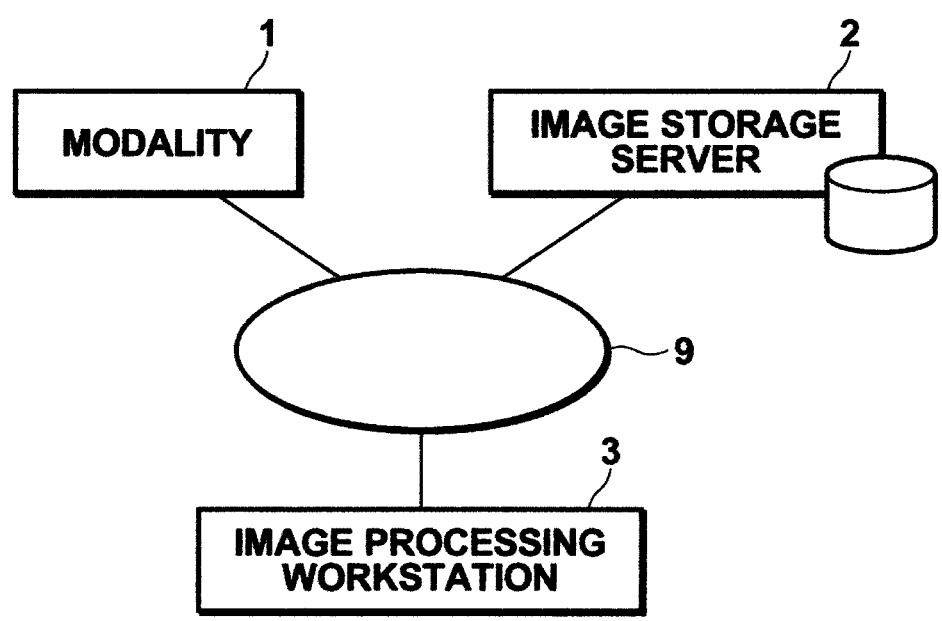
FIG. 1 is a schematic configuration diagram of a medical image diagnosis system in which a medical image diagnosis assisting apparatus according to an embodiment of the present invention is implemented.

FIG. 1 is a hardware configuration diagram of the medical image diagnosis system, illustrating an overview thereof. As shown in FIG. 1, the system includes modality 1, image storage server 2, and image processing workstation 3 are communicatably connected to each other via network 9.

Modality 1 includes an apparatus that images an inspection target region of a subject to generate image data representing a three-dimensional medical image of the region and outputs the image data by attaching auxiliary information defined in DICOM (Digital Imaging and Communication in Medicine) standard as image information. Specific examples of the apparatus include, for example, CT, MRI, and the like. In the present embodiment, a description will be made of a case in which three-dimensional image data representing a chest region of a human body to be examined are generated by scanning the human body with CT in a body axis direction.

Image storage server 2 is a computer for storing medical image data, in a database, obtained by modality 1 and image data of a medical image generated by image processing in image processing workstation 3 and managing them, and includes a large capacity external memory unit and database management software (e.g., Object Relational Database (ORDB)).

Image processing workstation 3 is a computer that performs, in response to a request from a radiology reader, image processing (including image analysis) on medical image data obtained from modality 1 or image storage server 2 and displays a generated image. It is provided with known hardware devices, such as a CPU, a main storage unit, an auxiliary storage unit, an input/output interface, a communication interface, input devices (mouse, keyboard, and the like), a display device (display monitor), a data bus, and the like, and has a known operating system installed thereon. The medical image diagnosis assisting process is implemented in the image processing workstation 3 and the process is realized by executing a program installed from a recording medium, such as a CD-ROM or the like. Alternatively, the program may be a program installed after being downloaded from a storage unit of a server connected via a network, such as Internet or the like.

The storage format of image data and communication between each component of the system are based on the DICOM protocol or the like.

Figure 2:
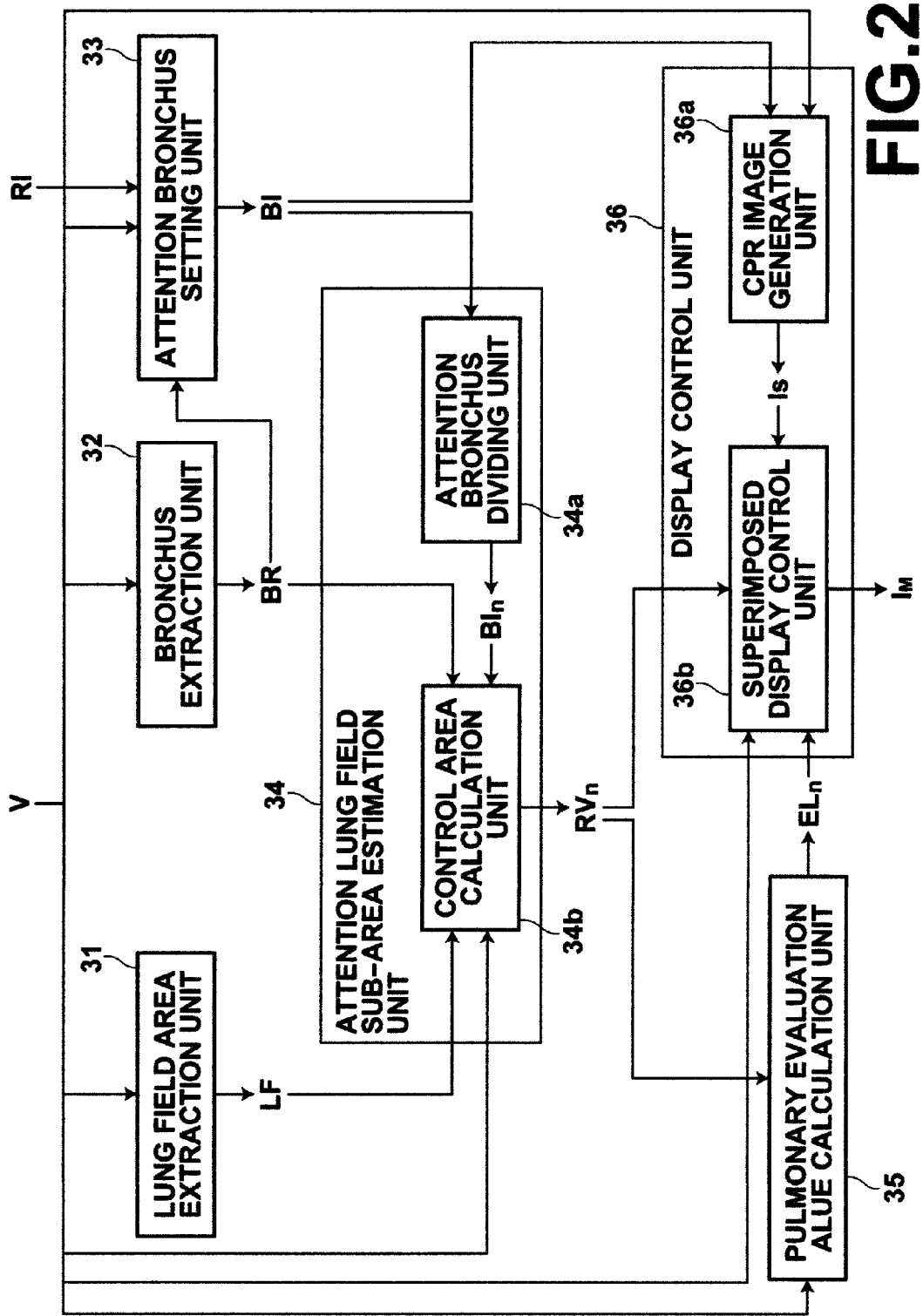
FIG. 2 is a block diagram schematically illustrating a configuration and a process flow for realizing a medical image diagnosis assisting function according to a first embodiment of the present invention.

FIG. 2 is a block diagram illustrating a portion of the function of image processing workstation 3 relevant to the medical image diagnosis assisting process according to the first embodiment of the present invention. As shown in FIG. 2, the medical image diagnosis assisting process according to the first embodiment of the present invention is realized by lung field area extraction unit 31, bronchus extraction unit 32, attention bronchus setting unit 33, attention lung field sub-area estimation unit 34, pulmonary evaluation value calculation unit 35, and display control unit 36. In FIG. 2, the three-dimensional medical image V, attention area RI, lung field area LF, bronchus structure BR, attention bronchus structure BI, attention bronchus sub-area $BI_n$, attention lung field sub-area $RV_n$, pulmonary evaluation value $EL_n$, CPR image $I_S$, and display image $I_M$ are data written into and read out from a predetermined memory area of image processing workstation 3 by each of the processing units described above.

Lung field area extraction unit 31 extracts a lung field area LF of a subject using each of a plurality of axial cross-sectional images constituting a three-dimensional medical image V as input. For example, as the lung field area LF is an area having a pixel value corresponding to the CT value of air, an air area in the subject may be extracted as the lung field area after discriminating between the air area around the subject and the subject area by performing threshold processing on each axial cross-sectional image.

Bronchus extraction unit 32 extracts a bronchus structure BR of the subject using the three-dimensional medical image V as input. More specifically, region growing is performed to extract a mass of pixels within a bronchus area, then a thinning process is performed on the extracted bronchus area, and based on the obtained thin line representing a bronchus, each pixel on the thin line is classified into an end point, an edge (side), or a branch point, whereby tree-structure data representing the bronchus can be obtained. Further, characteristic amounts, such as bronchus diameter at each pixel on the thin line, length of each edge (length between branches of the bronchus), and the like, may also be stored as the tree-structure data, as required.

Attention bronchus setting unit 33 sets an attention bronchus structure BI in a bronchus structure BR. More specifically, attention bronchus setting unit 33 causes an image generated from the three-dimensional medical image V to be displayed on the display device of image processing workstation 3, and receives a user operation specifying an attention area RI which includes a bronchus structure BR. Then, attention bronchus setting unit 33 sets a bronchus structure in the attention area RI as the attention bronchus structure BI based on a tree-structure of the bronchus structure BR.

Attention lung field sub-area estimation unit 34 includes attention bronchus dividing unit 34a and control area calculation unit 34b.

Figure 3A:
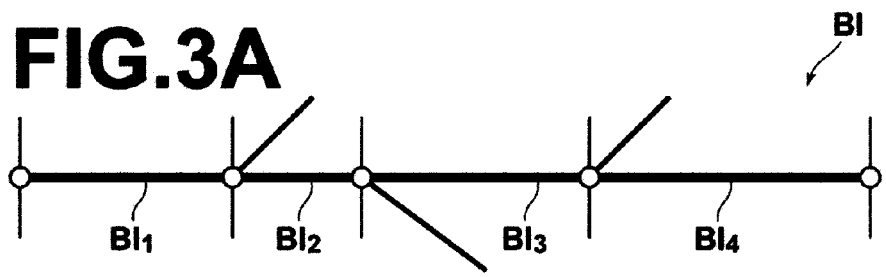
FIG. 3A schematically illustrates a method of dividing an attention bronchus structure.

Attention bronchus dividing unit 34a divides the attention bronchus structure BI into a plurality of attention bronchus sub-areas $BI_n$ (n is a suffix identifying each attention bronchus sub-area). More specifically, as schematically illustrated in FIG. 3A, the attention bronchus structure BI is divided with respect to each branch point and divided edges are referred to as sub-areas $BI_1$, $BI_2$, $BI_3$, and $BI_4$ respectively.

Figure 4:
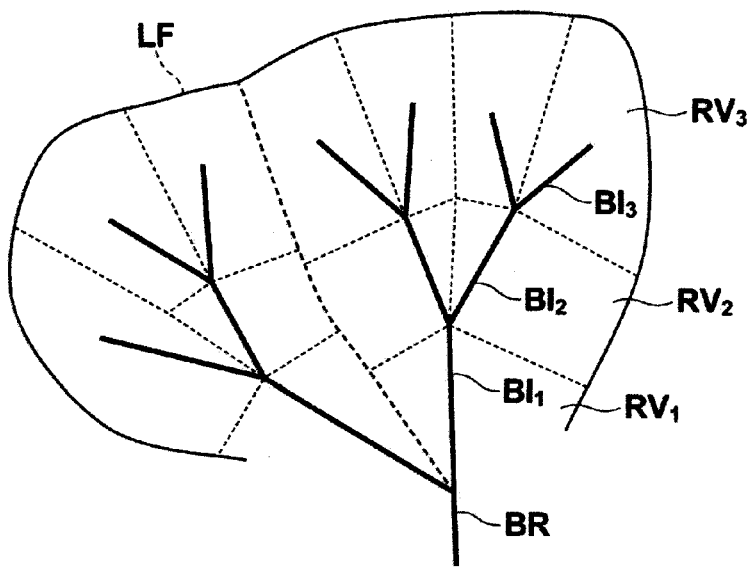
FIG. 4 schematically illustrate a control area with respect to each attention bronchus structure sub-area.

Control area calculation unit 34b performs three-dimensional Voronoi division using a bronchus structure BR as the kernel point mass to obtain a control area of each attention bronchus sub-area $BI_n$ constituting the attention bronchus structure BR. Here, the obtained control area is estimated to be an attention lung field sub-area $RV_n$ functionally associated with the attention bronchus sub-area $BI_n$. More specifically, as schematically illustrated in FIG. 4, control area calculation unit 34b identifies one of branches constituting the bronchus structure BR located closest to each pixel in the lung field area LF, that is, identifies by which of the bronchus branches each pixel in the lung field area LF is controlled. As a result, an area controlled by the same bronchus branch is determined to be the control area of the bronchus branch. This yields a control area with respect to each attention bronchus sub-area $BI_n$, i.e., the attention lung field sub-area $RV_n$. (For details, refer to "Quantification of shrinkage of lung lobes in chest CT images using the 3D Voronoi division and application to tumor discrimination" by Y. Hirano et al., [Online], JMIT $20^{th}$ annual meeting proceedings, pp. 315-316, July 2001, [Date of Retrieval: Nov. 20, 2009], Internet <URL: http://mase.itc.nagoya-u.ac.Jp/~hirano/Papers/JAMIT2001.pdf>.)

Pulmonary evaluation value calculation unit 35 calculates a pulmonary evaluation value $EL_n$ with respect to each attention lung field sub-area $RV_n$ based on the three-dimensional medical image V. Here, a degree of emphysema is used as the pulmonary evaluation value $EL_n$. More specifically, using the three-dimensional medical image V as input, pulmonary evaluation value calculation unit 35 determines an area of the lung field area LF where a pixel value is less than a predetermined threshold value (threshold value of −960 HU is preferable for a non-contrast enhanced CT image) as an emphysema area. (For details, refer to a literature "Quantitation of emphysema by computed tomography using a "density mask" program and correlation with pulmonary function tests" by M. Kinsella et al., Chest, Vol. 97, pp. 315-321, 1990.) Then, based on a volume of the determined emphysema area, an emphysema ratio is obtained as the pulmonary evaluation value $EL_n$ by emphysema ratio=volume of emphysema area in the attention lung field sub-area $RV_n$/volume of the attention lung field sub-area $RV_n$.

Display control unit includes CPR image generation unit 36a and superimposed display control unit 36b.

CPR image generation unit 36a generates a CPR image $I_S$ by a known straightened CPR based on the three-dimensional medical image V and attention bronchus structure BI.

Figure 5:
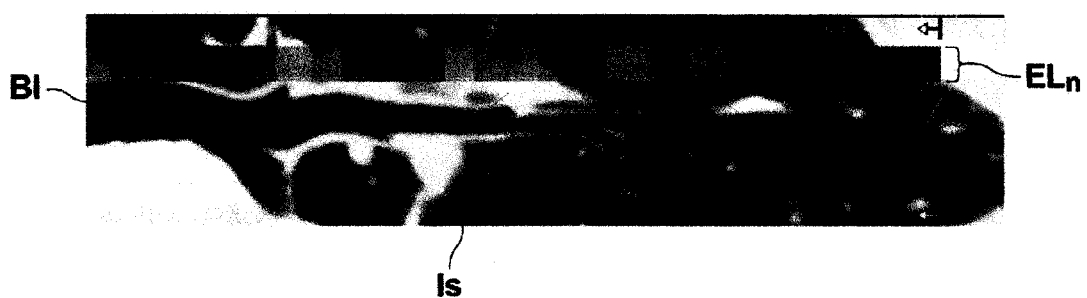
FIG. 5 illustrates an example of superimposed image generated in the first embodiment.

Superimposed display control unit 36b generates a superimposed image $I_M$ in which the CPR image $I_S$ and the pulmonary evaluation value $EL_n$ of each attention lung field sub-area $RV_n$ functionally associated with each attention bronchus sub-area $BI_n$ in the CPR image are superimposed such that the correspondence relationship between each pulmonary evaluation value $EL_n$ and each attention bronchus sub-area $BI_n$ is visually recognizable, and causes the display device of image processing workstation 3 to display the superimposed image $I_M$. FIG. 5 shows an example of image $I_M$ displayed in a superimposed manner, in which a color map of colors and density values allocated according to the pulmonary evaluation value $EL_n$ of each attention bronchus sub-area $BI_n$ is displayed in the CPR image $I_S$ superimposed on a position away from the core line of the attention bronchus structure BI by a predetermined distance. Here, the color map is superimposed such that each color separation boundary position in the color map, i.e., the boundary position between a map element allocated to a pulmonary evaluation value $EL_N$ and a map element allocated to a pulmonary evaluation value $EL_{N+1}$ corresponds to each boundary position between attention bronchus sub-areas $BI_n$ of the attention bronchus structure BI, i.e., the boundary position between an attention bronchus sub-area $BI_N$ and an attention bronchus sub-area $BI_{N+1}$ in a left-right direction of the CPR image $I_S$.

Figure 7:
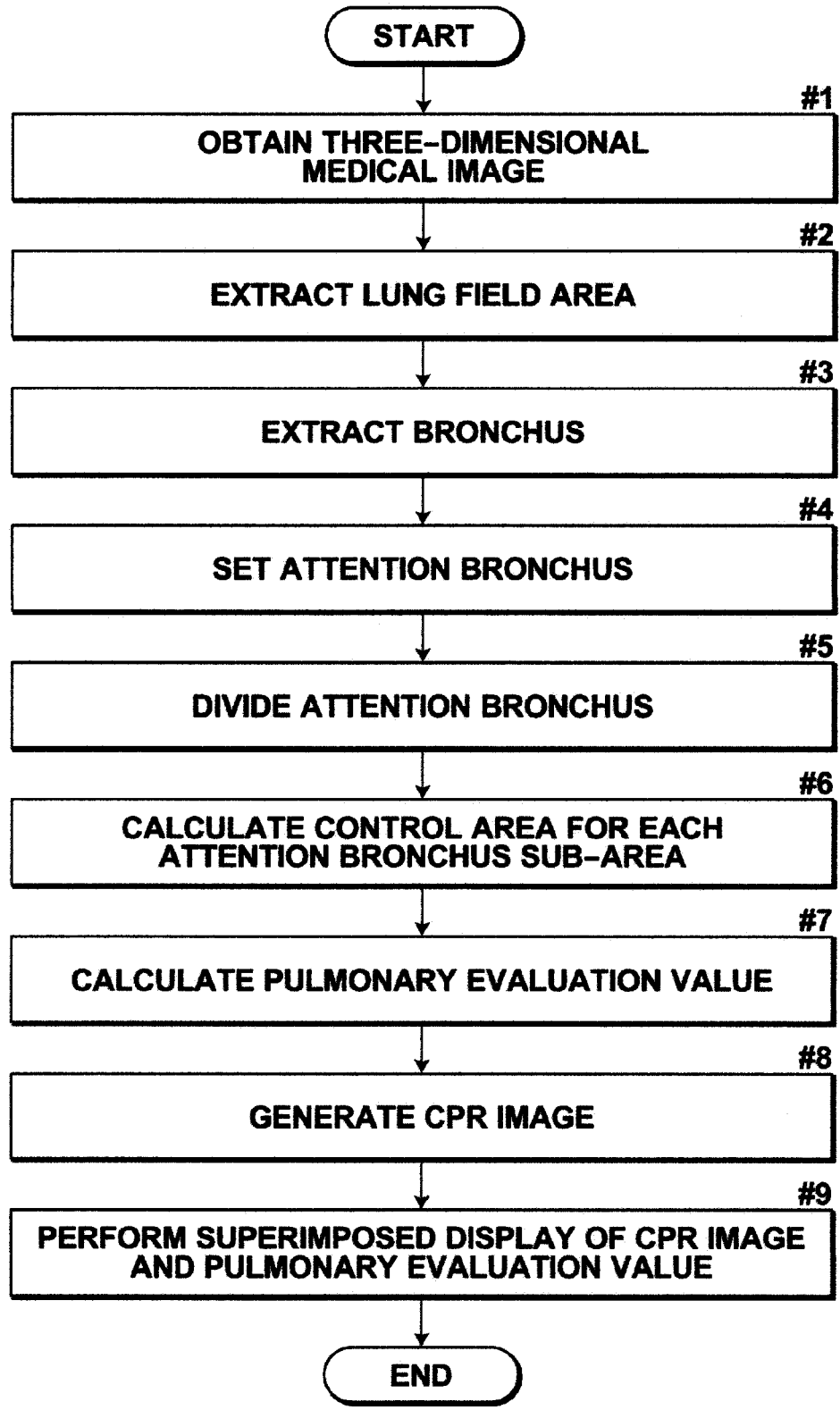
FIG. 7 is a flowchart illustrating a flow of image diagnosis assisting process using the medical image diagnosis system according to the first embodiment of the present invention.

A flow of image diagnosis using the medical image diagnosis assisting process according to the first embodiment of the present invention will now be described. FIG. 7 is a flowchart illustrating a flow of user operation, calculation processing, display processing, and the like performed under the execution of medical image diagnosis assisting software according to the first embodiment of the present invention.

First, image data of a three-dimensional medical image V is obtained (#1). The three-dimensional medical image V is an image captured by modality 1 and stored in image storage server 2 based on an examination order from a doctor of a requesting department. The user makes a request for obtaining a processing target three-dimensional medical image data V by operating a terminal operation interface of a known ordering system implemented in image processing workstation 3. In response to the operation, image processing workstation 3 sends a request for retrieval of the three-dimensional medical image data V to image storage server 2. Then, image storage server 2 obtains the processing target three-dimensional medical image data V by performing database searching and sends the data to image processing workstation 3. Image processing workstation 3 obtains the three-dimensional medical image data V sent from image storage server 2.

In image processing workstation 3, lung field area extraction unit 31 extracts a lung field area LF of the subject using each of a plurality of axial cross-sectional images constituting the three-dimensional medical image V as input (#2) and bronchus extraction unit 32 extracts a bronchus structure BR using the three-dimensional medical image V as input (#3).

Thereafter, attention bronchus setting unit 33 receives a user operation specifying an attention area RI in the bronchus structure BR and, based on the tree-structure of the bronchus structure BR, sets the bronchus structure in the specified attention area RI as an attention bronchus structure BI (#4), and attention bronchus dividing unit 34a of attention lung field sub-area estimation unit 34 divides the attention bronchus structure BI set by attention bronchus setting unit 33 into a plurality of attention bronchus sub-areas $BI_n$ (#5). Then, using the three-dimensional medical image V as input, control area calculation unit 34b of attention lung field sub-area estimation unit 34 obtains a control area with respect to each attention bronchus sub-area $BI_n$, i.e., attention lung field sub-area $RV_n$ based on the lung field area LF extracted by lung field area extraction unit 31 and the bronchus structure BR extracted by bronchus extraction unit 32 (#6). Further, based on the three-dimensional medical image V, pulmonary evaluation value calculation unit 35 calculates a volume ratio (emphysema ratio) of an emphysema area in each attention lung field sub-area $RV_n$ as a pulmonary evaluation value $EL_n$ (#7).

Finally, in display control unit 36, CPR image generation unit 36a generates a CPR image $I_S$ based on the three-dimensional medical image V and attention bronchus structure BI (#8) and superimposed display control unit 36b generates a superimposed image $I_M$ in which a color map representing pulmonary evaluation values $EL_n$ is superimposed on the CPR image $I_S$ generated by CPR image generation unit 36a and causes the display device of image processing workstation 3 to display the superimposed image $I_M$.

In the first embodiment of the present invention, by examining the superimposed image $I_M$ generated by the series of processing described above, the lung may be locally evaluated based on the functional relationship between the attention bronchus structure BI, which is a local region of the bronchus, and the adjacent lung field area. That is, highly accurate pulmonary image diagnosis may be made by considering the association with a bronchus.

Further, as shown in FIG. 5, display control unit 36 causes a color map of pulmonary evaluation values $EL_n$ to be displayed on a position where the color map does not overlap with the attention bronchus structure BI in the CPR image $I_S$, so that, while checking pulmonary evaluation values $EL_n$, the state of each attention bronchus sub-area $BI_n$ corresponding to each pulmonary evaluation value $EL_n$ may be observed in the CPR image $I_S$, thereby contributing to the improvement of diagnostic efficiency and accuracy.

Still further, the CPR image $I_S$ may extensively represent an attention bronchus structure BI, so that the morphology of attention bronchus structure BI and pulmonary evaluation values $EL_n$ may be examined and evaluated over a wide range at a glance.

Figure 8:
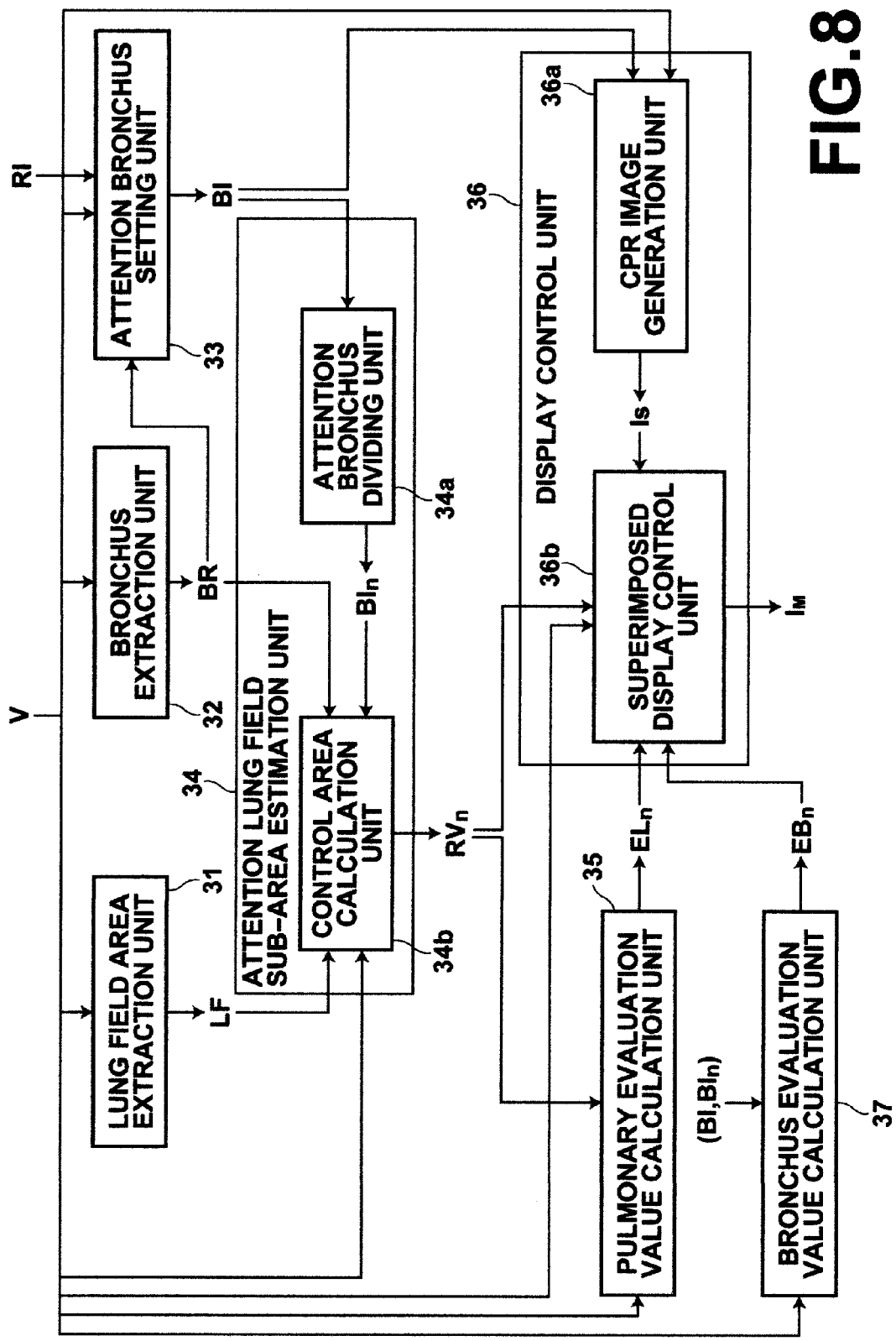
FIG. 8 is a block diagram schematically illustrating a configuration and a process flow for realizing a medical image diagnosis assisting function according to a second embodiment of the present invention.

FIG. 8 is a block diagram illustrating a portion of the function of image processing workstation 3 relevant to the medical image diagnosis assisting process according to a second embodiment of the present invention. As shown in FIG. 8, the structure of the second embodiment of the present invention is identical to that of the first embodiment (FIG. 2), other than that bronchus evaluation value calculation unit 37 is additionally provided.

Bronchus evaluation value calculation unit 37 measures an inner diameter of the attention bronchus structure BI based on the three-dimensional medical image V and outputs the value as a bronchus evaluation value $EB_n$. More specifically, an inner diameter of the attention bronchus structure BI is measured in a cross-sectional image orthogonal to the core line of the attention bronchus structure BI at each of a plurality of points on the core line. Here, an average value of inner diameter is measured with respect to each attention bronchus sub-area $BI_n$.

Figure 10:
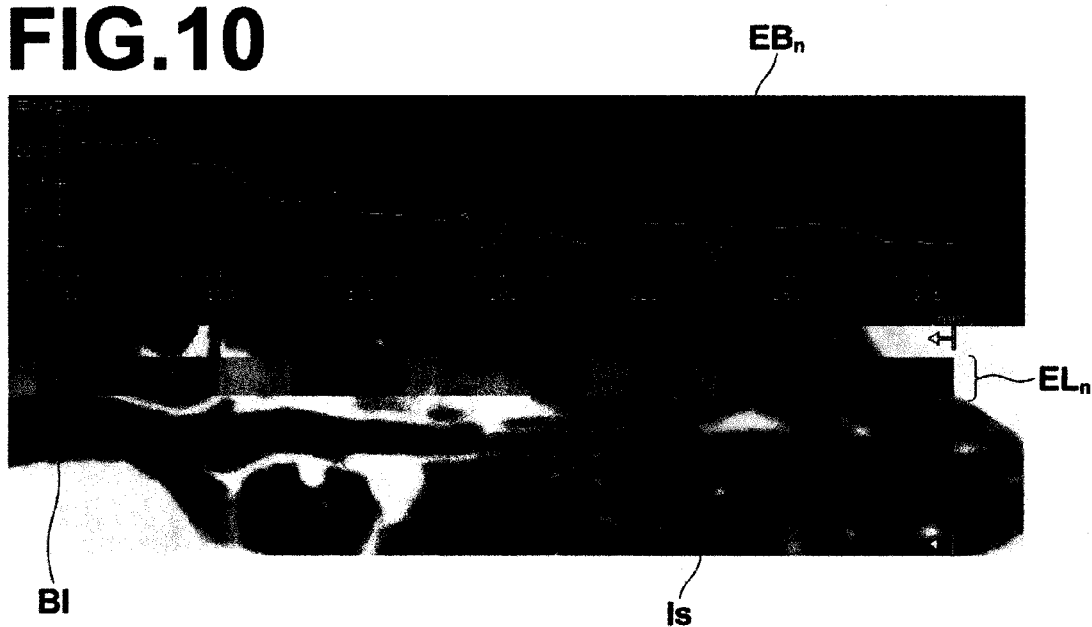
FIG. 10 illustrates an example of superimposed image generated in the second embodiment.

Further, superimposed display control unit 36b generates a superimposed image $I_M$ in which the CPR image $I_S$ and pulmonary evaluation values $EL_n$ and bronchus evaluation values $EB_n$ are superimposed such that the correspondence relationship between each pulmonary evaluation value $EL_n$/bronchus evaluation value $EB_n$ and each attention bronchus sub-area $BI_n$ in the CPR image $I_S$ is visually recognizable, and causes the display device of image processing workstation 3 to display the superimposed image $I_M$. FIG. 10 shows an example of image $I_M$ displayed in a superimposed manner, in which a color map of pulmonary evaluation values $EL_n$ is superimposed on the CPR image $I_S$, as in FIG. 5, and a line chart representing variations in the bronchus evaluation value $EB_n$ is displayed superimposed on a position away from the core line of the attention bronchus structure BI by a predetermined distance such that each evaluation value corresponds to the position of each attention bronchus sub-area $BI_n$ in the CPR image $I_S$ in a left-right direction of the CPR image $I_S$.

Figure 9:
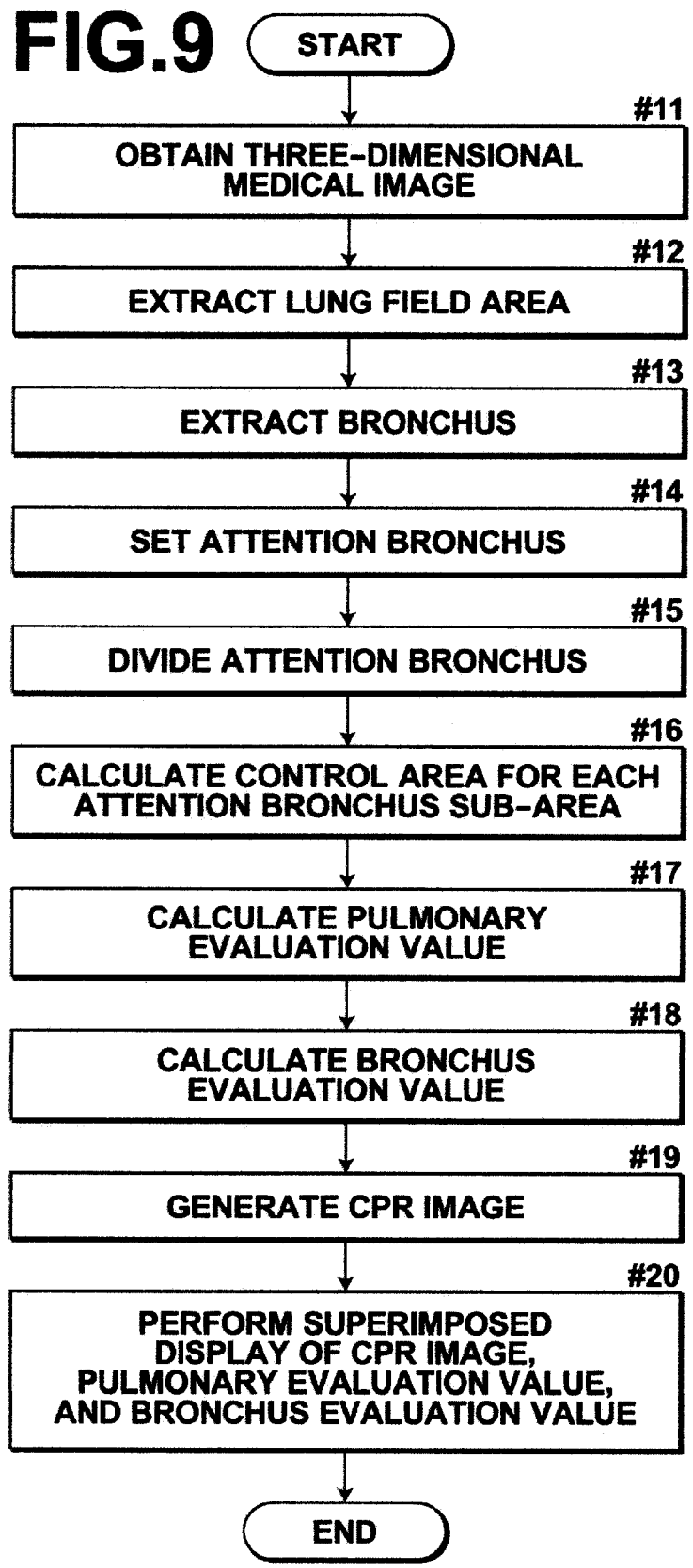
FIG. 9 is a flowchart illustrating a flow of image diagnosis assisting process using the medical image diagnosis system according to the second embodiment of the present invention.

FIG. 9 is a flowchart illustrating a flow of user operation, calculation processing, display processing, and the like performed under the execution of medical image diagnosis assisting software according to the second embodiment of the present invention. As shown in FIG. 9, the flow is identical to that of the first embodiment (FIG. 7) from step #11 to step #17. Then, bronchus evaluation value calculation unit 37 measures a bronchus evaluation value $EB_n$ representing an inner diameter of the attention bronchus structure BI based on the three-dimensional medical image V (#18). Then, as in the first embodiment, CPR image generation unit 36a generates a CPR image $I_S$ based on the three-dimensional medical image V and the attention bronchus structure BI (#19), and superimposed display control unit 36b generates a superimposed image $I_M$ in which a color map representing pulmonary evaluation values $EL_n$ and a graph representing bronchus evaluation values $EB_n$ are superimposed on the CPR image $I_S$ generated by CPR image generation unit 36a and causes the display device of image processing workstation 3 to display the superimposed image $I_M$ (#20).

As described above, in the second embodiment of the present invention, by examining the superimposed image $I_M$ generated by the series of processing described above, the relationship between the evaluation of emphysema degree based on the pulmonary evaluation value $EL_n$ and the inner diameter of the bronchus based on the bronchus evaluation value $EB_n$ may be understood easily while examining the state of attention bronchus sub-areas $BI_n$ in the CPR image $I_S$, whereby highly accurate diagnosis may be performed more efficiently.

The embodiments described above are illustration purposes only and should not be construed as limiting the scope of the technical scope of the present invention.

It should be appreciated that various modifications and changes made to the system configurations, processing flows, module structures, specific processing contents, and the like in the embodiments described above without departing from the spirit of the present invention are included in the scope of the present invention.

For example, with respect to the system configurations, a description has been made of a case in which various types of processing in FIG. 2 are performed by a single image processing workstation 3, but the system may be configured such that the various types of processing is distributed to a plurality of workstations and performed in cooperation with each other.

With respect to the processing flows, step #8 in the flowchart in FIG. 7 according to the first embodiment may be performed at any timing after step #4 and before step #9 or in parallel with steps #5 to #7. Likewise, in the second embodiment, step #19 in the flowchart in FIG. 9 may be performed at any timing after step #14 and before step #20 or in parallel with steps #15 to #18. Further, steps #17 and #18 may be performed in reverse or parallel.

With respect to specific processing contents, lung field extraction unit 31 may extract a lung field area LF by other known extraction methods, such as the method proposed by the present applicant in Japanese Unexamined Patent Publication No. 2008-253293.

Likewise, bronchus extraction unit 32 may employ various types of known bronchus extraction methods other than that described above (e.g., a literature "A Method for Extraction of Bronchus Regions from 3D Chest X-ray CT Images by Analyzing Structural Features of the Bronchus" by T. Kitasaka et al., Form a, Vol. 17, pp. 321-338, 2002). If, at that time, a tree-structure is obtained simultaneously with the extraction, the obtained tree-structure may be used directly in the subsequent processing without performing a thinning process. Further, bronchus extraction unit 32 may be configured to extract a pulmonary artery area as a bronchus area. Alternatively, bronchus extraction unit 32 may be configured to extract both the bronchus and pulmonary artery areas, and with respect to a peripheral portion of the bronchus, a portion of the pulmonary artery area from a point in the pulmonary artery area nearest to a peripheral portion of the extracted bronchus to a peripheral portion of the pulmonary artery may be extracted as a bronchus area connecting to the peripheral portion of the bronchus. Note that the pulmonary artery can be extracted by a known method. For example, tree-structure data representing the pulmonary artery can be obtained by receiving a user setting operation of a seed point representing the pulmonary artery, extracting a mass of pixels within the pulmonary artery area by region growing using the seed point set by the user, performing a thinning process on the extracted pulmonary artery area, and based on the connection of obtained thin lines representing the pulmonary vessel, classifying each pixel on the thin lines into an end point, an edge (side), or a branching point (for details, refer to a literature "Trial of branch base tree structure model construction for blood vessel geometric representation" by D. Kobayashi et al., [Online], RIKEN, Japan, RIKEN symposium, Digitization and database construction research of organism shape information, pp. 84-92, Mar. 3, 2005, [Date of Retrieval: Jan. 6, 2010], Internet <URL: http://www.comp-bio.riken.jp/keijyo/products/2005_1_files/kobay ashi_print.pdf>, and a literature "Automated Classification of Pulmonary Artery and Vein from Chest X-ray CT Images by Tree Structure Analysis" by S. Nakamura et al., Technical Report of IEICE, MI, Japan, Vol. 105, No. 580, pp. 105-108, Jan. 21, 2006, [Date of Retrieval: Nov. 20, 2009], Internet <URL: http://www.murase.nuie.nagoya-u.ac.jp/~ide/res/paper/J05-kenkyukai-snake-1.pdf>).

Attention bronchus setting unit 33 may receive a user operation specifying an attention point, instead of receiving a user operation specifying an attention area RI, and set a bronchus from the specified point to a peripheral portion as the attention bronchus structure BI.

Figure 3B:
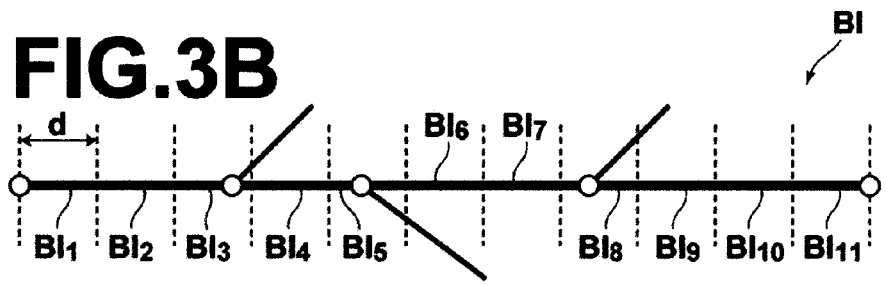
FIG. 3B schematically illustrates another method of dividing an attention bronchus structure.

Instead of dividing the attention bronchus structure BI at branching points as shown in FIG. 3A, attention bronchus dividing unit 34a may be configured to divide the attention bronchus structure BI into attention bronchus sub-areas $BI_n$ ($BI_1$ to $BI_{11}$ in FIG. 3B) at a predetermined distance d (e.g., 10 mm) or the interval may be changed depending on the position of the bronchus (depending on where the position is in the range from base to periphery of the bronchus).

Instead of obtaining an attention lung field sub-area $RV_n$ with respect to each attention bronchus sub-area $BI_n$, control area calculation unit 34b may be configured to obtain one attention lung field sub-area $RV_n$ for a group of a plurality of attention bronchus sub-areas $BI_n$ or to further break down one attention bronchus sub-area $BI_n$ into sub-area portions and obtain an attention lung field sub-area $RV_n$ with respect to each of the broken down portions of the attention bronchus sub-area $BI_n$. Further, the attention lung field sub-area $RV_n$ may be obtained based on characteristic amounts, such as the diameter of the bronchus and the like, and pixel values stored in the tree structure data of the bronchus structure BR, as well as the distance between a pixel in the lung field area LF and the bronchus When an attention lung field sub-area $RV_n$ is obtained by performing Voronoi division on the entire lung field area LF, attention lung field sub-area $RV_n$ may sometimes cross over a boundary of a plurality of lung lobes, so that control area calculation unit 34b may be configured to separate the lung field area LF into lung lobes (five lobes of right upper lobe, right middle lobe, right lower lobe, left upper lobe, left middle lobe, and left lower lobe) in advance and to calculate the attention lung field sub-area $RV_n$ within each lung lobe. Here, the separation method of lung lobes may be automatic or manual. As for the automatic separation method, any known method may be used, such as a method in which locations of interlobar fissures are roughly identified using structural information of trachea, bronchus, pulmonary blood vessel, then the interlobar fissures are extracted using density information, and lung lobes are separated based on the extracted interlobar fissures. (For details, refer to a literature "Development of the Procedure for Automatic Extracting Interlobar Fissures and its Performance Evaluation" by T. Hayashi et al., Technical Report of IEICE, MI, Medical Image, Vol. 103, No. 409, pp. 39-44, Oct. 31, 2003, [Date of Retrieval: Jan. 8, 2010], Internet, <URL: http://www.fjt.info.gifu-u.ac.jp/publication/328.pdf>.)

Further, control area calculation unit 34b may be configured to extract a pulmonary artery area by a known method, then to obtain a control area of a pulmonary artery area from a point in the pulmonary artery area nearest to a peripheral portion of the bronchus structure BR extracted by bronchus extraction unit 32 to a peripheral portion of the pulmonary artery by Voronoi division, and to combine the obtained control area with the attention lung field sub-area $RV_n$ functionally associated with the attention bronchus sub-area $BI_n$ to which the peripheral portion of the bronchus structure BR belongs. This may result in that the attention lung field sub-area $RV_n$ functionally associated with the attention bronchus sub-area $BI_n$ to which the peripheral portion of the bronchus structure BR belongs becomes relatively large, but the pulmonary artery runs near the center of anatomical sections of the lung (pulmonary sections, pulmonary sub-sections) so that the use of the peripheral portion of the pulmonary artery in estimating an attention lung field sub-area $RV_n$ corresponding to the attention bronchus sub-area $BI_n$ in the peripheral portion of the bronchus structure BR may prevent the attention lung field sub-area $RV_n$ corresponding to the peripheral portion of the bronchus structure BI from crossing over a boundary of anatomical sections of the lung even at a position in the lung field area away from the peripheral portion of the bronchus structure BI. This allows functional evaluations consistent with the anatomical structure of a lung to be made.

As for the evaluation value calculated by pulmonary evaluation value calculation unit 35, the following known items may be cited other than the emphysema ratio used in the embodiment described above.

(a) An emphysema cluster size in an attention lung field sub-area

As in the embodiment described above, an emphysema area is determined by threshold processing and a volume of each connected component (cluster) in the emphysema area is obtained. Further, a fractal dimension D is calculated with respect to each connected component (for details, refer to a literature "Complexity of terminal airspace geometry assessed by lung computed tomography in normal subjects and patients with chronic obstructive pulmonary disease" by M. Mishima et al., Proc. Natl. Acad. Sci. USA, Vol. 96, pp. 8829-8834, 1999).

(b) Perfusion parameters obtainable from time density curves obtained in a plurality of regions of interest in a CT perfusion analysis, such as pulmonary blood flow, pulmonary blood volume, mean transit time, local adjacent average density described in U.S. Pat. No. 7,715,608, and the like.

(c) Pixel values of a plurality of radiation images representing transmission/attenuation degrees of a plurality of radiation patterns having different energy distributions in a subject respectively. Alternatively, a difference in pixel value between a plurality of images (captured by emitting different energies from a plurality of radiation sources, captured by emitting radiation from one radiation source by changing the energy, captured by exposing, once, a plurality of radiation detectors stacked on top of each other via an additional filter, such as an energy separation filter to change the energy distribution of radiation transmitted through the subject by one exposure and detecting radiation of different energy distributions by the plurality of radiation detectors.

(d) Pixel values of pulmonary functional images obtained by CT and other modalities, such as PET, MRI, lung perfusion scintigraphy, lung ventilation scintigraphy, and the like.

(e) A difference in pixel value between a plurality of images before and after the administration of a contrast agent or a plurality of images captured at different times after the administration of a contrast agent.

(f) A local ventilation volume, such as a difference in pixel value between a plurality of ventilation images obtained between inhalation and exhalation or before and after inhalation of a predetermined gas (for details, refer to Japanese Unexamined Patent Publication No. 2005-028121).

(g) A displacement amount at each position in a lung field between inhalation and exhalation (refer to U.S. Pat. No. 7,286,694 filed by the present applicant). A displacement amount may be obtained with respect to each pixel in a bronchus or a control area and an average value or a maximum value may be used as the evaluation value.

(h) An amount of temporal variation of evaluation value obtained in each item above. A difference in evaluation value of each item described above obtained from a plurality of images/measurement values captured/measured at different times is used as the evaluation value.

Note that for those involving calculation between a plurality of images captured at different times, such as between inhalation and exhalation or captured by different modalities, the position of a subject or a structure is different between the images due to misalignment of the bodily position of the subject or cardiac/pulmonary contractions at the times of imaging. Therefore, it is necessary to perform position alignment processing in order to align the positional relationship. As for the position alignment processing, any known rigid or non-rigid registration method may be used. The non-rigid registration includes, for example, a method in which two corresponding points are specified by the user, a method that performs the alignment based on the image contrast without using a landmark, or the like (for details, refer to Japanese Unexamined Patent Publication No. 2005-028121 and a literature "Nonrigid Registration Using Free-Form Deformations: Application to Breast MR Images" by D. Rueckert et al., IEEE Transactions on Medical Imaging, Vol. 18, No. 8, pp. 712-721, 1999, and the like). Further, the bronchus extracted by bronchus extraction unit 32 may be used as the landmark.

Figure 6:
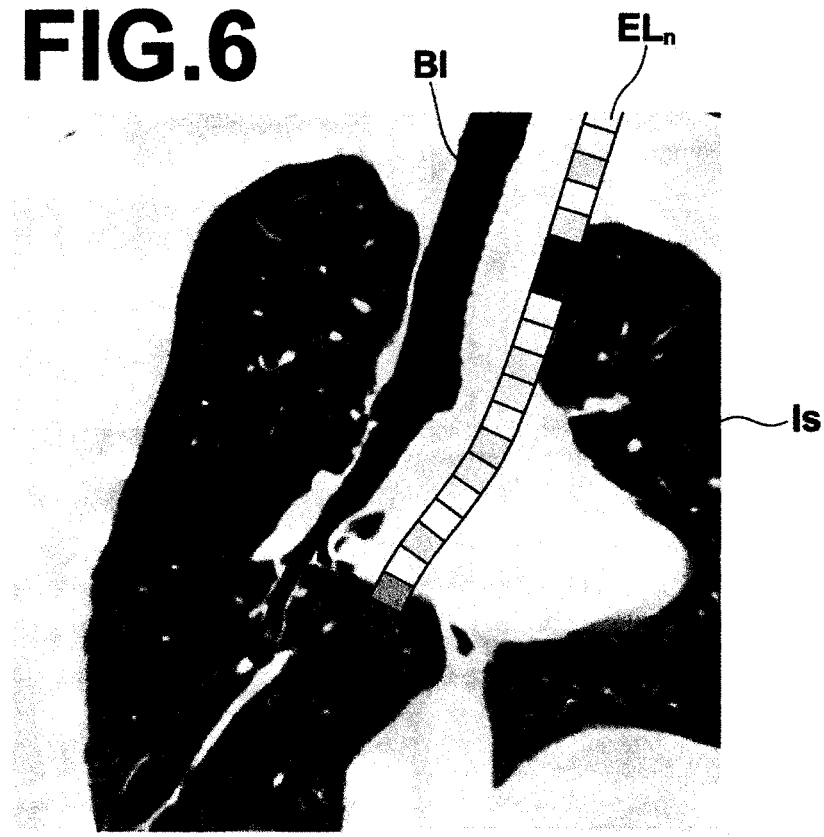
FIG. 6 illustrates another example of superimposed image generated in the first embodiment.

CPR image generation unit 36a may be configured to generate a CPR image $I_S$ by stretched CPR or projected CPR, instead of the straightened CPR. FIG. 6 illustrates an example in which a color map representing evaluation values $EL_n$ along an attention bronchus structure BI is superimposed on a CPR image $I_S$ generated by stretched CPR. Further, CPR image generation unit 36a may be replaced with another unit that generates another type of image representing morphology of an attention bronchus structure BI, such as volume rendering image, MIP image, or MPR image.

Figure 11:
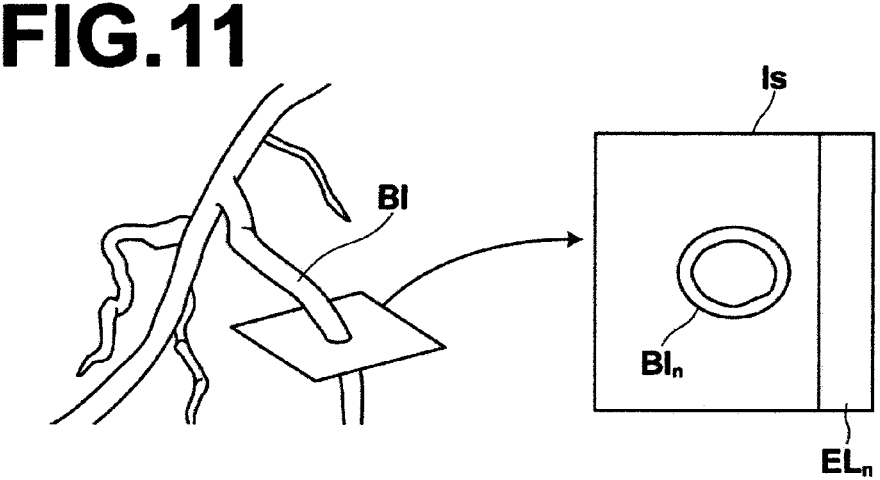
FIG. 11 illustrates another example of superimposed image generated in the second embodiment.

Superimposed display control unit 36b may be configured to display a color map and a graph of pulmonary evaluation values $EL_n$ and bronchus evaluation values $EB_n$ on each side of an attention bronchus structure BI in a CPR image $I_S$ respectively or on the core line of the attention bronchus structure BI in a superimposed manner, or to display color maps or graphs of pulmonary evaluation values $EL_n$ and bronchus evaluation values $EB_n$ outside of the CPR image $I_S$. Further, superimposed display control unit 36b may be configured to display a portion of the attention bronchus structure BI within a predetermined observation range and corresponding portions of color maps of pulmonary evaluation values $EL_n$ and bronchus evaluation values $EB_n$ and to change the observation range in response to a user operation for scrolling when performing a superimposed display. Still further, superimposed display control unit 36b may be configured to accept a specifying operation of an attention point on a CPR image $I_S$ and to display not only the superimposed display shown in FIG. 5, 6, or 10 but also a cross-sectional image representing a cross-section of the attention bronchus structure BI at the specified point or a pseudo three-dimensional image, such as a local volume rendering image representing the specified point and around thereof at a position different from that of the superimposed display or further superimposed on the CPR image in popup display. Otherwise, as illustrated in FIG. 11, display control unit 36 may be configured to accept a specifying operation of an attention point in a volume rendering image representing an attention bronchus structure BI to generate a cross-sectional image representing a cross-section of the attention bronchus structure BI at the specified point and to display color maps or graphs of pulmonary evaluation values $EL_n$ and bronchus evaluation values $EB_n$ in the generated cross-sectional image in a superimposed manner. In FIG. 11, a specifying operation of an attention point is accepted in a volume rendering image, but the specifying operation may be accepted in a CPR image. Further, a local pseudo three-dimensional image representing an attention point and around thereof may be used instead of a cross-sectional image.

The display form of pulmonary evaluation values $EL_n$ and bronchus evaluation value $EB_n$ may be other than the color map or graph described above. For example, if it is a case of emphysema evaluation values, a color map may be displayed only in an emphysema area in a CPR image in a superimposed manner.

Bronchus evaluation value calculation unit 37 may be configured to calculate a bronchus wall thickness, a bronchus lumen cross-sectional area, a bronchus wall cross-sectional area, a ratio of a bronchus wall cross-sectional area to a bronchus lumen cross-sectional area, an amount of temporal variation in each item described above, or the like as the bronchus evaluation value $EB_n$.

In the embodiments described above, the attention is focused on a bronchus, but an embodiment focusing on a pulmonary blood vessel instead of a bronchus may also be conceivable. That is, an arrangement may be adopted in which a lung field area and a pulmonary blood vessel structure are extracted from a three-dimensional medical image of a chest region, an attention pulmonary blood vessel structure is divided into a plurality of attention pulmonary blood vessel sub-areas, a lung field local sub-area functionally associated with each attention pulmonary blood vessel sub-area is estimated based on the pulmonary blood vessel structure, a pulmonary evaluation value is obtained for each estimated lung field local sub-area, and a pulmonary evaluation value of each lung field local sub-area functionally associated with each attention pulmonary blood vessel sub-area in a morphological image generated from the three-dimensional medical image representing morphology of at least a portion of the attention pulmonary blood vessel structure is superimposed on the morphological image in a manner that allows the correspondence relationship between each lung field evaluation value and each attention pulmonary blood vessel sub-area in the morphological image to be visually recognizable. In this case, the pulmonary blood vessel may be extracted by the known method described above by setting a seed point in the pulmonary blood vessel. Other processing steps may be carried out by replacing the term "bronchus" in the embodiments described above with the term "pulmonary blood vessel".

What is claimed is:

1. A medical image diagnosis assisting apparatus, comprising:
   a lung field area extraction means for extracting a lung field area from a three-dimensional medical image representing a chest region of a subject;
   a branch structure area extraction means for extracting a branch structure area from the three-dimensional medical image;
   a lung field local sub-area estimation means for dividing a branch structure local area representing a portion of the branch structure area into a plurality of branch structure local sub-areas and estimating a lung field local sub-area in the lung field area functionally associated with each divided branch structure local sub-area based on the branch structure area;
   a pulmonary evaluation value obtaining means for obtaining a pulmonary evaluation value of pulmonary function and/or morphology in each estimated lung field local sub-area; and
   a display control means for displaying, in a morphological image representing morphology of at least a portion of the branch structure local area generated from the three-dimensional medical image, the pulmonary evaluation value in each lung field local sub-area functionally associated with each branch structure local sub-area in the morphological image superimposed such that a correspondence relationship between the pulmonary evaluation value and the branch structure local sub-area in the morphological image is visually recognizable,
   wherein the display control means displays the pulmonary evaluation value as a color map, the color map including map elements, colors and density values of the map elements being allocated according to the pulmonary evaluation value of each of the branch structure local sub-areas, each boundary position between the map elements corresponding to each boundary position between the branch structure local sub-areas.

2. The medical image diagnosis assisting apparatus of claim 1, wherein the display control means is a means that displays the pulmonary evaluation value in the morphological image superimposed on a position not to overlap with the branch structure local area.

3. The medical image diagnosis assisting apparatus of claim 2, wherein the display control means is a means that displays the pulmonary evaluation value in the morphological image superimposed on a position away from a core line of the branch structure local area by a predetermined distance.

4. The medical image diagnosis assisting apparatus of claim 1, wherein the morphological image is an image representing morphology of the entirety of the branch structure local area.

5. The medical image diagnosis assisting apparatus of claim 1, wherein the morphological image is a CPR image representing the branch structure local area.

6. The medical image diagnosis assisting apparatus of claim 1, wherein the morphological image is an image that includes a lung field local sub-area functionally associated with at least a portion of the branch structure local area.

7. The medical image diagnosis assisting apparatus of claim 6, wherein the display control means is a means that displays the pulmonary evaluation value in the morphological image superimposed on a position not to overlap with the branch structure local area and the lung field local sub-area.

8. The medical image diagnosis assisting apparatus of claim 1, wherein: the apparatus further comprises a second evaluation value obtaining means for dividing the branch structure local area in the morphological image into a plurality of second branch structure local sub-areas and obtaining a second evaluation value, different from the pulmonary evaluation value, with respect to each second branch structure local sub-area; and the display control means is a means that further displays the second evaluation value of each second branch structure local sub-area superimposed on the morphological image such that correspondence relationship between the second evaluation value and the second branch structure local sub-area is visually recognizable.

9. The medical image diagnosis assisting apparatus of claim 8, wherein the display control means is a means that displays the second evaluation value in the morphological image superimposed on a position not to overlap with the pulmonary evaluation value of pulmonary function and/or morphology.

10. The medical image diagnosis assisting apparatus of claim 8, wherein the second evaluation value is an evaluation value of branch structure morphology.

11. The medical image diagnosis assisting apparatus of claim 10, wherein the second evaluation value is a measured value of the diameter of a branch structure in each of the second branch structure local sub-areas.

12. The medical image diagnosis assisting apparatus of claim 1, wherein the pulmonary evaluation value is an evaluation value representing a degree of emphysema in each of the lung field local sub-areas.

13. The medical image diagnosis assisting apparatus of claim 1, further comprising a branch structure local area setting means for setting the branch structure local area in the branch structure area.

14. The medical image diagnosis assisting apparatus of claim 1, wherein the branch structure is a bronchus.

15. The medical image diagnosis assisting apparatus of claim 14, wherein the branch structure area extraction means is a means that further extracts a pulmonary artery area to extract an area from a portion of the pulmonary artery area nearest to a peripheral portion of the extracted bronchus area to a peripheral portion of the pulmonary artery area as a bronchus area connecting to the peripheral portion of the extracted bronchus area.

16. The medical image diagnosis assisting apparatus of claim 14, wherein the lung field local sub-area estimation means is a means that further extracts a pulmonary artery area and estimates the lung field local sub-area with a portion of the pulmonary artery area from a point in the pulmonary artery area nearest to a peripheral portion of the bronchus extracted by the branch structure area extraction means to a peripheral portion of the pulmonary artery being deemed as a bronchus area connecting to the peripheral portion of the bronchus.

17. The medical image diagnosis assisting apparatus of claim 1, wherein the branch structure is a pulmonary blood vessel.

18. A medical image diagnosis assisting method, comprising:
- extracting a lung field area from a three-dimensional medical image representing a chest region of a subject;
- extracting a branch structure area from the three-dimensional medical image;
- dividing a branch structure local area representing a portion of the branch structure area into a plurality of branch structure local sub-areas and estimating a lung field local sub-area in the lung field area functionally associated with each divided branch structure local sub-area based on the branch structure area;
- obtaining a pulmonary evaluation value of pulmonary function and/or morphology in each estimated lung field local sub-area; and
- displaying, in a morphological image representing morphology of at least a portion of the branch structure local area generated from the three-dimensional medical image, the pulmonary evaluation value in each lung field local sub-area functionally associated with each branch structure local sub-area in the morphological image superimposed such that a correspondence relationship between the pulmonary evaluation value and the branch structure local sub-area in the morphological image is visually recognizable,
- wherein the pulmonary evaluation value is displayed as a color map, the color map including map elements, colors and density values of the map elements being allocated according to the pulmonary evaluation value of each of the branch structure local sub-areas, each boundary position between the map elements corresponding to each boundary position between the branch structure local sub-areas.

19. A non-transitory computer readable medium on which is recorded a medical image diagnosis assisting program for causing a computer to perform a method comprising:
- extracting a lung field area from a three-dimensional medical image representing a chest region of a subject;
- extracting a branch structure area from the three-dimensional medical image;
- dividing a branch structure local area representing a portion of the branch structure area into a plurality of branch structure local sub-areas and estimating a lung field local sub-area in the lung field area functionally associated with each divided branch structure local sub-area based on the branch structure area;
- obtaining a pulmonary evaluation value of pulmonary function and/or morphology in each estimated lung field local sub-area; and
- displaying, in a morphological image representing morphology of at least a portion of the branch structure local area generated from the three-dimensional medical image, the pulmonary evaluation value in each lung field local sub-area functionally associated with each branch structure local sub-area in the morphological image superimposed such that a correspondence relationship between the pulmonary evaluation value and the branch structure local sub-area in the morphological image is visually recognizable,
- wherein the pulmonary evaluation value is displayed as a color map, the color map including map elements, colors and density values of the map elements being allocated according to the pulmonary evaluation value of each of the branch structure local sub-areas, each boundary position between the map elements corresponding to each boundary position between the branch structure local sub-areas.

* * * * *

UNITED STATES PATENT AND TRADEMARK OFFICE
CERTIFICATE OF CORRECTION

PATENT NO. : 8,483,467 B2  
APPLICATION NO. : 13/017415  
DATED : July 9, 2013  
INVENTOR(S) : Osamu Mizuno Page 1 of 1

It is certified that error appears in the above-identified patent and that said Letters Patent is hereby corrected as shown below:

On the Title page, left column:

"(30)    Foreign Application Priority Data  
    Jan. 31, 2010 (JP) ................................ 2010-084388"

should be replaced with:

--(30)    Foreign Application Priority Data  
    Mar. 31, 2010 (JP) ................................ 2010-084388--

Signed and Sealed this  
Third Day of September, 2013

Teresa Stanek Rea  
*Acting Director of the United States Patent and Trademark Office*